US005661132A

United States Patent [19]
Eriksson et al.

[11] Patent Number: 5,661,132
[45] Date of Patent: Aug. 26, 1997

[54] WOUND HEALING

[75] Inventors: Elof Eriksson, Welesley; Christophe Andree, Boston, both of Mass.; William F. Swain, Madison; Michael D. Macklin, Middleton, both of Wis.

[73] Assignee: Auragen, Inc., Middleton, Wis.

[21] Appl. No.: 343,401

[22] Filed: Nov. 22, 1994

Related U.S. Application Data

[63] Continuation-in-part of Ser. No. 76,550, Jun. 11, 1993, abandoned, which is a continuation-in-part of Ser. No. 897,357, Jun. 11, 1992, Pat. No. 5,423,778, which is a continuation-in-part of Ser. No. 707,248, May 22, 1991, Pat. No. 5,152,757, which is a continuation of Ser. No. 451,957, Dec. 14, 1989, abandoned.

[51] Int. Cl.$^6$ .............................. A61K 48/00; C12N 15/00
[52] U.S. Cl. ...................... 514/44; 435/41; 435/172.3; 435/240.1; 435/240.2; 435/240.21; 435/240.23; 514/2
[58] Field of Search ........................... 536/22.1, 23.1, 536/24.1, 24.2; 435/252.3, 240.1, 320.1, 240.2; 514/44, 2; 424/93.21

[56] References Cited

U.S. PATENT DOCUMENTS

| | | | |
|---|---|---|---|
| 3,026,874 | 3/1962 | Stevens | 604/305 |
| 3,288,140 | 11/1966 | McCarthy | 604/289 |
| 3,580,254 | 5/1971 | Stuart | 604/290 |
| 3,814,097 | 6/1974 | Ganderson et al. | 604/304 |
| 4,304,866 | 12/1981 | Green et al. | 435/240.23 |
| 4,767,746 | 8/1988 | Catsimpoolas et al. | 514/25 |
| 4,788,971 | 12/1988 | Quisno | 128/743 |
| 4,847,193 | 7/1989 | Richards et al. | 435/6 |
| 4,868,116 | 9/1989 | Morgan et al. | 435/240.2 |
| 4,944,948 | 7/1990 | Uster et al. | 424/450 |
| 4,945,056 | 7/1990 | Sanford et al. | 435/172.1 |
| 4,980,286 | 12/1990 | Morgan et al. | 435/172.3 |
| 5,152,757 | 10/1992 | Eriksson | 604/305 |
| 5,262,128 | 11/1993 | Leighton et al. | 422/100 |

FOREIGN PATENT DOCUMENTS

| | | |
|---|---|---|
| 641061 | 8/1950 | United Kingdom. |
| 2210618 | 6/1989 | United Kingdom. |
| WO90/11092 | 10/1990 | WIPO. |
| WO92/15676 | 9/1992 | WIPO. |

OTHER PUBLICATIONS

Andree, C., et al., "In Vivo Transfer and Expression of a Human Epidermal Growth Factor Gene Accelerates Wound Repair," *Proc. Natl. Acad. Sci. USA*, 91:12188–12192 (1994).

Breuing, et al., "Healing of Partial Thickness Porcine Skin Wounds in a Liquid Environment," *Journal of Surgical Research* 52:50–58 (1992).

Eriksson, et al., "In Vivo Cell Culture Accelerates Reepithelialization," *Surgical Forum* XLII:670–673 (1991).

Garlick et al., "Retrovirus-Mediated Transduction of Cultured Epidermal Keratinocytes," *Journal of Investigative Dermatology* 97:824–829 (1991).

Juni, et al., "Controlled Drug Permeation. II. Comparative Permeability and Stability of Butamben and Benzocaine," *Chem. Pharm. Bull.* 25:1098–1100 (1977).

Kaufman, et al., "Topical Oxygen and Burn Wound Healing: A Review," *Burns* 9:169–173 (1983).

Majumdar, A., and P. Stroeve, "Diffusion of Local Anaesthetics Through Liquid Membranes," (1986).

Morgan et al., "Expression of an Exogenous Growth Hormone Gene by Transplantable Human Epidermal Cells," *Science* 237:1476–1479 (1987).

Rheinwald and Green, "Epidermal Keratinocytes: The Formation of Keratinizing Colonies from Single Cells," *Cell*, pp. 331–343 (1975).

Sporr, M.B., and A. B. Roberts, p. 86 in *Peptide Growth Factors and Their Receptors I*, Springer-Verlag, New York (1990).

Wilson et al., "Implantation of Vascular Grafts Lined with Genetically Modified Endothelial Cells," *Science* 244:1344–1346 (1989).

Wright, P. C., "Fundamentals of Acute Burn Care and Physical Therapy Management," *Physical Therapy* 64:1217–1231.

Marshall, Science, 269, 1995, 1050–1055.
Yang et al., PNAS, 87, 1990, 9568–9572.
Bell et al., Nuc. Acids Res., 14(21), 1986, 8427–8446.
Brown et al, J. Exp. Med., 163, 1986, 1319–1324.
Morgan et al, Science, 237, 1987, 1476–1479.
Flowers et al, PNAS, 87, 1990, 2349–2353.
Teumer et al, FASEB, 4, 1990, 3245–3250.

*Primary Examiner*—Jacqueline M. Stone
*Assistant Examiner*—Andrew Milne
*Attorney, Agent, or Firm*—Robins & Associates

[57] ABSTRACT

A DNA molecule encoding a secretable mature epidermal growth factor (EGF) polypeptide is delivered to a skin wound. The cells that take up the recombinant DNA construct express soluble EGF that is secreted into surrounding fluid. The presence of the EGF accelerates, by a statistically significant amount, the healing time of a wound treated in this manner.

The DNA molecule can be a genetic construction that expresses an EGF encoding portion that differs from the naturally occurring EGF precursor gene in that the only coding region retained from the precursor gene is that of the mature EGF polypeptide. Amino-terminal EGF-like repeats and the carboxy-terminal hydrophobic sequence that anchors natural EGF to the cell membrane are not present in the genetic construction.

19 Claims, 5 Drawing Sheets

WOUND HEALING

CROSS-REFERENCE TO RELATED APPLICATIONS

This application is a continuation-in-part of application Ser. No. 08/076,550 filed Jun. 11, 1993, now abandoned, which is a continuation-in-part of application Ser. No. 07/897,357, filed Jun. 11, 1992, now U.S. Pat. No. 5,423,778, which is a continuation-in-part of application Ser. No. 07/707,248, filed May 22, 1991, now U.S. Pat. No. 5,152,757, which is a continuation of application Ser. No. 07/451,957, filed Dec. 14, 1989, now abandoned.

FIELD OF THE INVENTION

The present invention relates generally to the field of healing and treatment of wounds, burns, tumors and other skin diseases and disorders, and relates in particular to the direct delivery into skin cells of a genetic construct that encodes a polypeptide having epidermal growth factor activity, and the subsequent secretion of the polypeptide into wound fluid for improved healing of such diseases and disorders.

BACKGROUND OF THE INVENTION

Epidermal growth factor (EGF) is recognized as a particularly useful treatment additive in wound treatment systems because of its role in promoting growth of epidermal skin tissue. Naturally occurring mature EGF is a 53 amino acid long polypeptide produced in vivo as the processed product of a very large (1200 amino acids long) precursor protein.

Early wound-healing systems introduced purified mature EGF as a treatment additive directly into wounds. However, the cost of treatment with mature EGF is high since the polypeptide has a short half-life in wounds. In addition, it is difficult to purify, store and administer large quantities of natural mature EGF for use in a wound treatment system as a result of its lability.

More recently, in vitro cultured skin cells such as keratinocytes and fibroblasts, some of which had been genetically modified, have been introduced into the wound-bathing fluid during treatment. These introduced cells repopulated wounded skin sites and secreted growth factors and other nutritive substances that enhance wound healing.

The concept of protecting a wound from the environment and using fluid to protect a wound is known. For example, a comprehensive treatment system for enhancing the healing of wounds, burns, skin diseases and the like is described in U.S. Pat. No. 5,152,757. The treatment system therein described includes a chamber that surrounds the wound and portals for introduction of treatment fluids and for extraction of wound fluid for monitoring and analysis. A user of the treatment system has control of various treatment variables including temperature, osmotic pressure, pH, ionic concentrations and oxygen content. Also, a user can select particular treatment additives, as indicated.

An alternate approach is desired that facilitates improved wound healing, yet eliminates the need for in vitro cell culture or for purification of EGF. What is desired is a method for delivering stable, appropriately processed EGF to epidermal cells without the difficulties that have accompanied prior efforts.

SUMMARY OF THE INVENTION

The present invention is summarized in that wound healing accelerates after transfer into a wound of a DNA molecule that encodes secretable mature epidermal growth factor (EGF).

In a first aspect, the invention is a method for accelerating wound healing that includes the steps of delivering a non-naturally occurring gene encoding secretable mature EGF directly into a plurality of cells at a wound site, isolating the wound site from the surrounding environment and allowing the host cells that have taken up the gene to express and secrete the non-natural EGF protein from the host cells into the extracellular fluid, thereby providing the cells at the wound site with a supply of a protein having cell growth-enhancing properties that is sufficient to accelerate the rate of wound healing.

In a second aspect, the invention is a genetic construct that encodes a mature EGF polypeptide that includes only a small portion of the full-length EGF precursor gene. In particular, the construct includes that portion that encodes the mature EGF polypeptide but not the portions that encode several upstream EGF-like repeats and glycosylation sites. The genetic construct does not include the hydrophobic transmembrane domain of the EGF precursor gene downstream of the mature EGF-encoding portion. The DNA sequence that encodes mature EGF is placed onto a genetic expression construct under the transcriptional control of an upstream promoter active in animal epidermal cells. The genetic expression construct also includes a polyadenylation site downstream from the mature EGF gene portion for efficient expression in eukaryotes and RNA processing signals to facilitate RNA splicing and transport to the cytoplasm. The genetic construct can encode additional structural or regulatory elements that can include, without limitation, a selectable marker gene, other transcriptional or translational enhancer elements, introns, or other amino acids encoded by, for example, the multicloning site of the parent construct.

In a third aspect, the invention is further summarized in that the EGF gene is delivered directly into skin cells located at the site of a wound.

It is an object of the present invention to provide a method for accelerating healing of skin wounds that does not require an externally applied source of purified EGF protein.

It is another object of the present invention to provide an expressible genetic construct that encodes a mature EGF protein that is secreted from target cells.

It is an advantage of the present invention that it overcomes the art-recognized difficulty in delivering exogenous EGF to cells at a wound site.

It is another advantage of the present invention that accelerated wound healing is achieved without the need to provide purified EGF to cells at a wound site.

It is yet another advantage of the present invention that the source of EGF activity is prepared in DNA form rather than in protein form. DNA is stable and inexpensive to obtain and to purify. In contrast, mature EGF protein is more expensive to obtain and to purify.

It is another advantage of the present invention to provide a method for accelerating wound healing wherein genetic material is delivered directly into cells at the wound site.

Other objects, features, and advantages of the present invention will become apparent upon consideration of the following specification read in conjunction with the accompanying drawings.

DETAILED DESCRIPTION OF THE INVENTION

A method for accelerating the healing of skin wounds in an animal includes the steps of exposing target cells at a wound site, delivering a DNA molecule that expresses a mature processed epidermal growth factor (EGF) into a plurality of the cells, isolating the wound site from the external environment and allowing the cells that have taken up the DNA molecule to secrete the mature growth factor into the extracellular fluid whereupon wound repair is accelerated.

All that is required of an EGF coding region is that the coding region encode a protein that enhances cell growth after delivery into target cells. A non-naturally occurring EGF-encoding DNA fragment useful in the present invention encodes only the small mature EGF-encoding portion of the gene that encodes the long EGF precursor protein. The EGF gene does not contain the multiple repeated EGF-like repeats that are encoded in the natural EGF precursor gene upstream of the mature protein, and does not include the transmembrane domain found downstream of the mature protein on the natural precursor gene. The EGF encoded by a DNA molecule within the present invention is soluble, that is, secreted from the host cell into the extracellular fluid where it becomes available to other cells at the wound site.

The EGF-encoding portion is obtained or derived from an animal gene encoding a member of the EGF family of proteins and is preferably from a human source. The EGF family of proteins includes proteins of the class that interact with or bind to the EGF receptor to enhance cell growth. The class includes, among others, TGF-alpha from any animal. The sequence of a full length human EGF precursor gene clone has been published. The DNA encoding mature EGF can also be synthesized in vitro using techniques known to the art and using the published DNA sequence as a guide. Complementary pairs of oligonucleotides of appropriate sequence to encode mature EGF are readily created and may be amplified using PCR and hybridized together to form DNA molecules useful in the present invention.

Alternatively, the EGF-encoding sequence can be obtained from any other non-human animal that produces EGF. For example, EGF and TGF are known to be produced by mice. The murine and human EGF precursor genes are about 66% identical in sequence and the mature proteins from the two species are 70% identical.

It may be possible to further truncate the DNA molecule disclosed herein that encodes the mature EGF amino acid chain, at either its 5' or 3' end or both, while still maintaining accelerated healing activity in the encoded protein. As is detailed below, healing can be monitored visually or biochemically by observing the rate of wound healing.

It is also understood that the exact nucleotide sequence of the DNA used need not be exactly as set forth herein. Rather, one skilled in the art will recognize that certain silent changes to the nucleic acid sequence have no effect on the amino acid encoded by a particular triplet. Even changes to certain amino acids do not affect, or only somewhat affect, the EGF activity of the encoded protein. The invention is intended to include the truncated natural EGF DNA having the nucleic acid sequence described herein, as well as all altered, varied and modified forms of the disclosed DNA. These can include but are not limited to substantially homologous DNA fragments having additions, deletions, and point mutations, relative to the disclosed nucleic acid sequence. A substantially homologous DNA fragment is one wherein the fragment encodes a polypeptide that accelerates the rate of wound healing in skin after delivery, even if such DNA differs in nucleic acid sequence or encodes a protein that differs in amino acid sequence from the DNA fragment or protein disclosed herein. Interspecies comparisons of mature EGF genes from humans and mice have demonstrated that even when the DNA sequences are only 70% homologous, functional equivalence is maintained. Even DNA sequences of as little as 60% or 50% homology to the human sequence could still retain EGF wound-healing biological activity.

A non-naturally occurring mature EGF encoding genetic expression construct contains, in 5' to 3' order, a promoter active in an animal host, a DNA fragment that encodes a polypeptide having a cell growth-stimulating activity encoded by a portion of the precursor gene that encodes natural EGF in animals, particularly in mammals, and a poly A addition sequence that directs the addition of a poly A tail to mRNA produced from the genetic construct template. It is also advantageous to provide an upstream secretory signal peptide-encoding sequence on the genetic construct in the same reading frame as the EGF portion, to promote secretion of the mature EGF protein.

As noted above, the DNA fragment may be obtained from other species or may be synthesized or may be a derivative of a natural or synthetic DNA molecule. Of course, if the gene encoding an EGF protein is engineered into a genetic construct for delivery into a host of a species other than that from which the gene derives, an immune response may occur after gene transfer. However, one skilled in the art will understand that by modifying the nucleic acid sequence of the mature EGF portion of the delivered gene, it is possible to destroy or eliminate undesired antigenic sites.

Given the similarity among EGF-encoding genes, it is also possible to avoid immune system conflicts by utilizing an isospecific EGF gene in a genetic construction. An isospecific gene is a donor gene recovered from the recipient species. This may be accomplished in non-human species by using the human gene to probe the genetic material of the other species for homologous EGF-encoding genes.

In forming the genetic construct, the mature EGF gene is provided with such termini as will permit it to be cloned in-frame into a mammalian expression vector downstream (3') of the promoter. By in-frame it is intended that the codon reading frame of the non-natural EGF protein of the expression vector is the same as that of natural EGF and that the sequences encoding the signal peptide and the EGF portion are in the same reading frame. The termini may be restriction enzyme sites naturally present in the EGF-encoding DNA or may be added in the form of linkers, or may be blunt-ended as appropriate for cloning into an expression vector. One or more non-EGF amino acids in the non-natural EGF protein may be encoded by, for example, the polylinker DNA into which the EGF gene is cloned or by a gene segment that encodes a secretory signal peptide. These amino acids have been shown to have no effect upon the EGF activity of the encoded protein product. Many promoter sequences are known to actively promote transcription of DNA in animal cells and any such promoter would be useful in a genetic expression construct within the present invention when placed 5' of the mature EGF encoding DNA fragment. An adequate promoter is any that promotes a sufficient level of transcription of a mature EGF gene in a target cell to yield a sufficient number of translatable transcripts to encode sufficient mature EGF polypeptide to accelerate wound healing when compared to healing in control animals. In particular, animal virus promoters such as the cytomegalovirus immediate early promoter and retroviral long terminal repeat promoters, such as the Rous sarcoma virus promoter, can be used in the present invention. The poly A addition sequence can be any one that directs the addition of a poly A tail to mRNA made from the expression construct template. Poly A addition sequences are widely distributed in eukaryotic genomes, since all transcribed genes are generally followed by such a sequence. A poly A addition sequence from the bovine growth hormone gene is conveniently used in a construct that expresses mature EGF.

It is understood that the regulatory sequences used to control gene expression may be modified to allow more precise control over production of the EGF or more responsiveness to particular physiologic needs of the healing wound.

Figure 1:
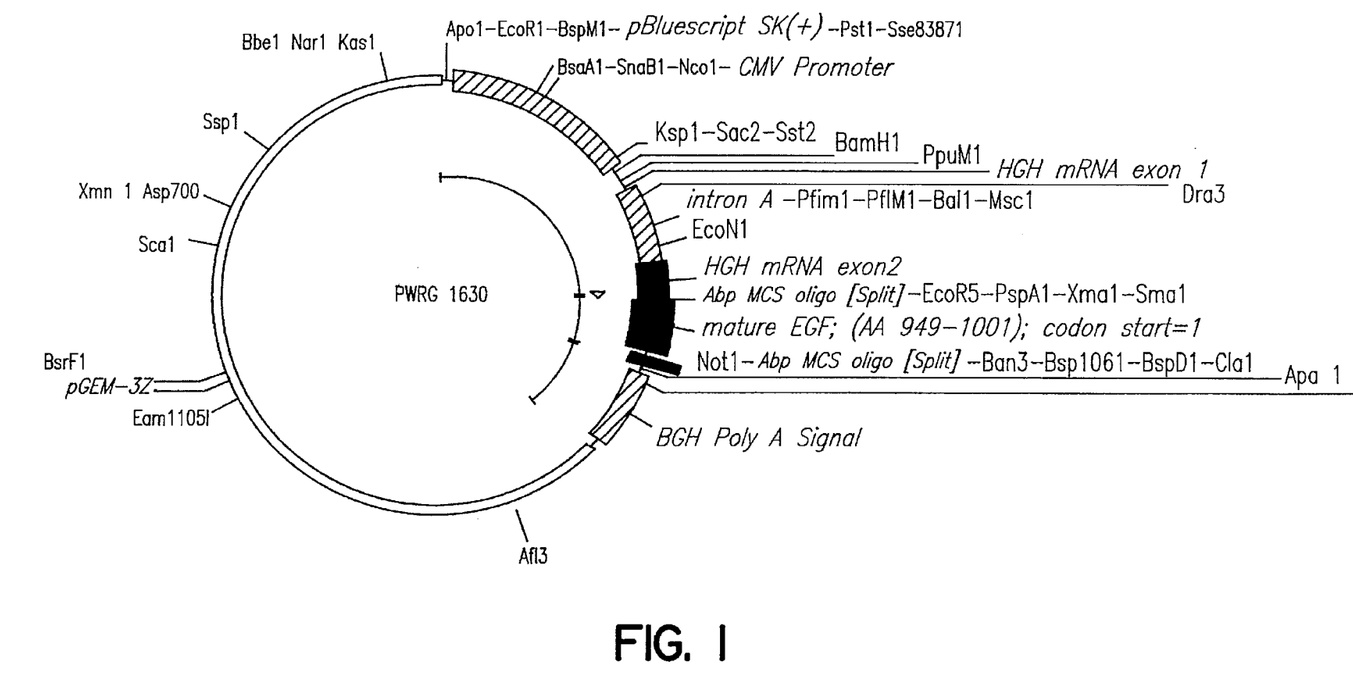
FIG. 1 depicts a schematic map of genetic expression construct pWRG1630.

A schematic map of pWRG1630, an exemplary plasmid genetic construction within the scope of the present invention, is shown in FIG. 1.

Introduction of Genetic Material

The target cells into which the mature EGF-expressing DNA is intended to be delivered are skin cells of human and non-human animals, preferably into mammalian skin. It is therefore expected that the invention will have utility in both human and veterinary therapies where improved wound healing is desired. The invention may be applied to rapidly healing wounds or to more chronic wounds such as non-healing ulcers, keloids, hypertrophic scars and malignant and non-malignant epidermal diseases. The nature of the wound that one desires to treat can influence the choice of gene delivered from among the known genes that encode particular cell growth enhancing proteins. It may be preferable to deliver genes for short-term expression, particularly when the invention is directed to wound healing in skin. Since skin cells are constantly sloughing off the surface, it is expected that long term expression will not be a concern.

The EGF-expressing DNA is delivered directly into dividing cells of the epidermis of the skin. The method of delivering the EGF DNA into the target cells is not believed to be critical. It is preferred that the EGF DNA be delivered using accelerated particle technology, because the accelerated particle approach facilitates DNA transfer to a higher proportion of cells than other methods.

Figure 2:
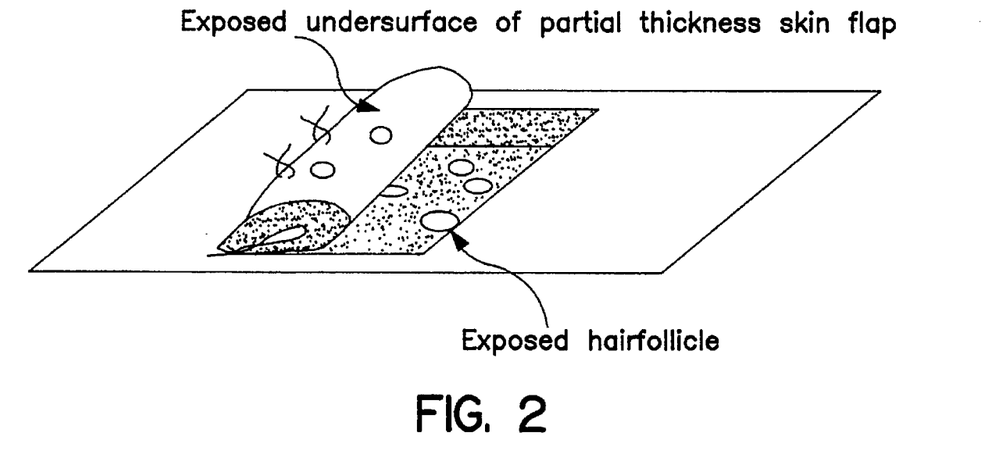
FIG. 2 is a schematic depiction of a partial thickness wound.

The following protocol can be utilized for direct in vivo gene transfer by particle acceleration to achieve systemic expression of the transferred EGF gene. Loose skin and tissues are removed and the area surrounding the wound is prepared to receive a dressing or wound chamber. As is shown in FIG. 2, target cells located in the hair follicles deep to the epidermal-dermal junction may be exposed by creating a flap of epidermis where the deep portion of the flap contains the basal layer of the epidermis. Alternatively, genes can be transferred directly into suitable wounds at desired depths without creating a flap by adjusting the delivery voltage.

The genetic material is then introduced into the target cells. Briefly, the EGF-encoding DNA is co-precipitated with carrier particles, preferably gold particles, of an appropriate size and shape to enter cells at high velocity after particle acceleration. Preferred particles are gold spheres of between 1 and 3 microns in diameter. During co-precipitation, the DNA coats the surface of the particles. The coated particles are precipitated in ethanol, washed, resuspended and reversibly deposited on a carrier surface for delivery into a target. The carrier surface can be a flexible sheet, such as a Mylar sheet, or other surface.

Without regard to the type of apparatus used, the deposited particles are then accelerated toward the target. Particle acceleration may be achieved by electric spark discharge, as described in U.S. Pat. No. 5,015,580, which is incorporated herein by reference, or by a gas-driven apparatus. The optimal delivery voltage in an electric spark discharge apparatus depends upon the target animal. Experience has indicated that lower voltages are appropriate for mice and monkeys than for pigs. It has been found that when an electric spark discharge type particle acceleration apparatus is used in pigs a discharge voltage of 25 kV is preferred, although voltages in the range of 15 to 35 kV are adequate to deliver genetic material into skin cells without damaging skin tissue. It has also been found that delivery of between 300 ng and 1.5 µg of DNA per $cm^2$ of target yields the highest EGF levels in wound fluid, and show the best healing activity. Thus, these amounts are preferred. A most preferred amount is 740 ng/$cm^2$. It is noted that the average amount of DNA per $cm^2$ may be non-uniform across the entire field.

Although particle acceleration is the preferred method for delivering EGF DNA into target cells, DNA could also be delivered using a viral vector, such as a retrovirus, adenovirus, or papillomavirus vector, to infect cells at the wound site. Viral delivery methods are less preferred because of the risk of unexpected and undesired genetic recombination with endogenous proviral DNA and because viral entry may be less efficient than particle acceleration. Lipid-mediated gene transfer has also been described in the art as another means for delivering genetic material into cells. See Felgner, P. L., et al., Lipofection: An Efficient, Lipid Mediated DNA-Transfection Procedure, PNAS USA, 84:7413–7417 (1987). Lipid-based products can be provided as skin creams containing microscopic liposome spheres with trapped genetic material therein. Other methods for delivering genetic material into skin cells include pretreatment of skin with a pore-inducing agent such as DMSO followed by direct application of genetic material. Direct topical application, however, is less preferred since it may disrupt wound healing and may deliver the growth factor farther from the true target cells.

In these methods the wound can be exposed in a wound chamber and the gene, in an appropriate vector for viral or plasmid transfer, may be introduced into the chamber.

Although gene transfer efficiency and expression vary at different skin sites, it is believed that routine optimization of delivery methods into a wound at any location on the skin surface would result in wound healing of the type disclosed herein. It is possible that certain modifications to the gene delivery protocol may be desirable to accommodate wounds of particular sizes or depths or variations in skin condition at particular target sites. Because of the depth control offered by particle acceleration methods, DNA can be targeted to the keratinocyte layer by adjusting the delivery force, even if no skin flap is created. At 25 kV delivery force, the average particle delivery depth is 60 µm in wounds. In intact epidermis, penetration is deeper (100–200 µm) when a 25 kV delivery force is used.

After gene transfer, the flap can be released to restore contact between the exposed, treated skin layers. The treated cells of the wound are isolated from the external environment both to keep the EGF localized at the wound site and to keep deleterious agents such as pathogens and dirt out of the wound. The wound site is preferably covered in a fluid-filled wound treatment chamber that keeps the wound moist and allows the fluid in the chamber to be monitored visually and biochemically during treatment. U.S. Pat. No. 5,152,757, which is incorporated herein by reference, describes one such wound treatment chamber that may be used in conjunction with the present invention. The patent also describes ways in which additives and therapeutics can be added to the wound treatment chamber and ways to monitor wound healing progress visually and biochemically. Other methods for monitoring a wound or keeping a wound clean and moist known to those skilled in the art of treating skin wounds may also be employed if use of a wound chamber is not possible or feasible.

The present invention will be more fully understood by reference to the following Examples, which are intended to be merely exemplary of the invention. In the Examples, pigs have been used as a model recipient for the EGF expression construct. Pigs are the standard animal model for extrapolation to human skin because porcine skin resembles human skin in several respects, including turnover time.

EXAMPLES

1. Construction of Plasmid Encoding Mature EGF Polypeptide.

Bacteriophage λgt10EGF116 (ATCC 59956), which includes a nearly full length human EGF gene obtained as a cDNA, was cleaved with SmaI and SnaBI. The phage was described by Bell, et al., *N.A.R.* 14:8427 (1986). Digestion of the λ clone with these enzymes excises the entire coding region of the EGF precursor. The fragment generated is blunt-ended. Synthetic NotI linkers were ligated to the ends of the EGF fragment. The fragment was digested with NotI to generate terminal overhangs and was ligated into NotI-cut plasmid pWRG1628. pWRG1628 includes a mammalian expression cassette wherein the promoter is a human cytomegalovirus immediate early promoter ($CMV_{ie}$) positioned 5' to an SV40 DNA fragment that contains intron splice donor and acceptor sites. The intron is followed downstream by a polylinker that includes a unique NotI cloning site. Downstream from the polylinker is an SV40 polyadenylation and 3' end processing signal portion.

The pWRG1628 mammalian expression vector bearing the precursor EGF coding region in its NotI cloning site was designated pWRG1629. To obtain a useful quantity of a DNA subfragment that encodes the coding sequence for mature EGF from pWRG1629, the portion of pWRG1629 lying between a pair of synthetic oligonucleotides was amplified using the Polymerase Chain Reaction (PCR). The synthetic oligonucleotide PCR primers were MA 1 (5'-TCAATAGTGACTCTGAATGTCCCC-3') and MA 2 (5'TCAGCGCAGTTCCCACCACTTCAG-3'). MA 1 and MA 2 are listed as SEQ ID NO: 1 and SEQ ID NO: 2, respectively. The MA 1 primer includes at its 5' end two additional nucleotides not found in the native mature EGF coding sequence. These nucleotides were added so that the fragment produced would maintain an appropriate reading frame when inserted into a T-tailed HpaI site of an expression vector in a subsequent cloning step. At the 3' end of MA 2, three nucleotides (ACT) not complementary to the natural EGF gene were added so that a termination codon (UGA) would be introduced in the amplified DNA generated during PCR. During amplification of the coding region fragment, the termination codon is added just downstream of the mature EGF coding sequence.

The amplified mature EGF encoding fragment was ligated into the HpaI site of the polylinker of pAbP2 to produce a plasmid designated pWRG1630, shown in FIG. 1 and presented as SEQ ID NO: 3. The expression cassette portion of plasmid pAbP2 contains the $CMV_{ie}$ transcriptional promoter (nucleotides 216 to 834 of Genbank Accession No. K03104), a 5' portion of the human growth hormone (hGH) gene that includes the hGH translation initiation codon, the hGH secretory signal peptide sequence, hGH intron 1 (nucleotides 274–686 of Genbank Accession No. J00148 K00612), a polylinker for in-frame fusion of heterologous coding sequences, and the polyadenylation and 3'-end processing signals from the bovine growth hormone (BGH) gene (from pRc/CMV, available from Invitrogen, Inc.). The backbone of pAbP2 is a pGEM3 vector. The HpaI-cut blunt ends of the vector had been pretreated with the Stoffel fragment of Taq polymerase which, in the presence of excess T, adds single T nucleotides to the 3' ends of nucleic acid strands. The sequence at the 5' junction between the polylinker and the EGF fragment was determined. It was revealed that there was neither a T tail on the vector portion nor the TC bases at the fragment's 5' end that had been expected because of the two base terminal addition on MA1. Thus, while it was expected that an additional in-frame codon (TTC encoding phenylalanine) would have formed during the cloning process, no such codon was formed. It is believed by the inventors that a weak exonucleolytic activity present in the reaction mix may have caused these terminal nucleotides to be clipped off. In any event, the empirically determined sequence shows that the desired reading frame was maintained. According to our experimental data, the amino acid sequence of the protein outside of the EGF portion has little or no bearing on the EGF activity of interest.

An intron of hGH origin is spliced out of the mRNA produced from the pWRG1630 template. The first exon that precedes the splice site encodes only three amino acids. The remainder of the 93 amino acid long protein product is encoded by the second exon. The protein product encoded by pWRG1630 (SEQ ID NO: 4) includes, from its amino end to its carboxyl end, the 26 amino acid long hGH secretory signal peptide, a novel 14 amino acid peptide portion encoded in part by the hGH DNA and in part by the polylinker of pAbP2, and a 53 amino acid long mature EGF portion. The mature EGF portion corresponds to the 53 amino acids of the naturally occurring mature EGF peptide. A signal peptide cleavage site is located between amino acids 26 and 27, which is the expected cleavage site of the hGH secretory signal peptide.

2. Use of pWRG1630 in Wound Healing System

Copies of pWRG1630 DNA, in various amounts, were loaded onto gold beads which were subsequently coated onto a Mylar carrier sheet. The DNA concentration ranged from 1.0 to 10.0 micrograms per milligram of gold. The gold beads ranged in diameter from 1 to 3 microns.

The coating step was performed using standard procedures. Briefly, a desired amount of pWRG1630 DNA was coprecipitated with gold beads using calcium chloride/spermidine. The precipitates were ethanol precipitated, washed once in ethanol, and resuspended in ethanol at 3 mg gold per ml. A desired amount of resuspended DNA-coated gold beads were gently deposited in 320 µl on each Mylar carrier sheet and allowed to settle onto the sheet. The ethanol was decanted and residual ethanol was allowed to evaporate. The coated Mylar sheet was dried. Dried, coated Mylar sheets were used without further preparation in an electric spark discharge type particle acceleration device of a type described in U.S. Pat. No. 5,015,580.

Partial thickness wounds in the skin of laboratory pigs were experimentally induced by creating a flap of epidermis using a Padgett® dermatome where the deep portion of the flap contains the basal layer of the epidermis. A schematic depiction of a partial thickness wound is shown in FIG. 2. The exposed wound surface contained the portion of the hair follicles with the stem cell keratinocytes.

The dried, DNA-coated gold particles were delivered by particle acceleration (25 kV discharge) into the partial thickness wounds. Each wound was covered with an adhesive vinyl wound chamber containing 1.2 ml of isotonic saline with 100 units per ml of penicillin and 100 µg/ml of streptomycin.

As is set forth in greater detail below, EGF activity is detectible for about ten days in wound fluid after particle mediated gene transfer of pWRG1630 into partial thickness wounds. The presence of mature EGF after direct delivery of an EGF gene into target cells decreases healing times of the induced partial thickness wounds.

a. Titration of pWRG1630 DNA

Gold beads ranging in diameter from 1 to 3 microns were separately co-precipitated with copies of pWRG1630 DNA molecules at 1.0, 2.5, 5.0, or 10.0 µg of DNA per mg of gold. Each sample of DNA-coated particles was re-suspended and 0.32 ml of each was pipetted onto a mylar carrier sheet of 3.24 cm². Table 1 reports the amount of DNA and gold delivered per cm² of target at each DNA concentration. Approximately 960 µg of coated gold were deposited on each 3.24 cm² carrier sheet.

TABLE 1

| DNA loading ratio | ng DNA/ cm² of target |
| --- | --- |
| 1.0µg/mggold | 296 |
| 2.5 | 741 |
| 5.0 | 1480 |
| 10.0 | 2960 |

Independent experiments were performed on two pigs. On the skin of a single pig, a sufficient number of wounds were induced to permit six sites to be targeted for each DNA concentration. In addition, six saline control samples containing no DNA were also delivered.

Figure 3:
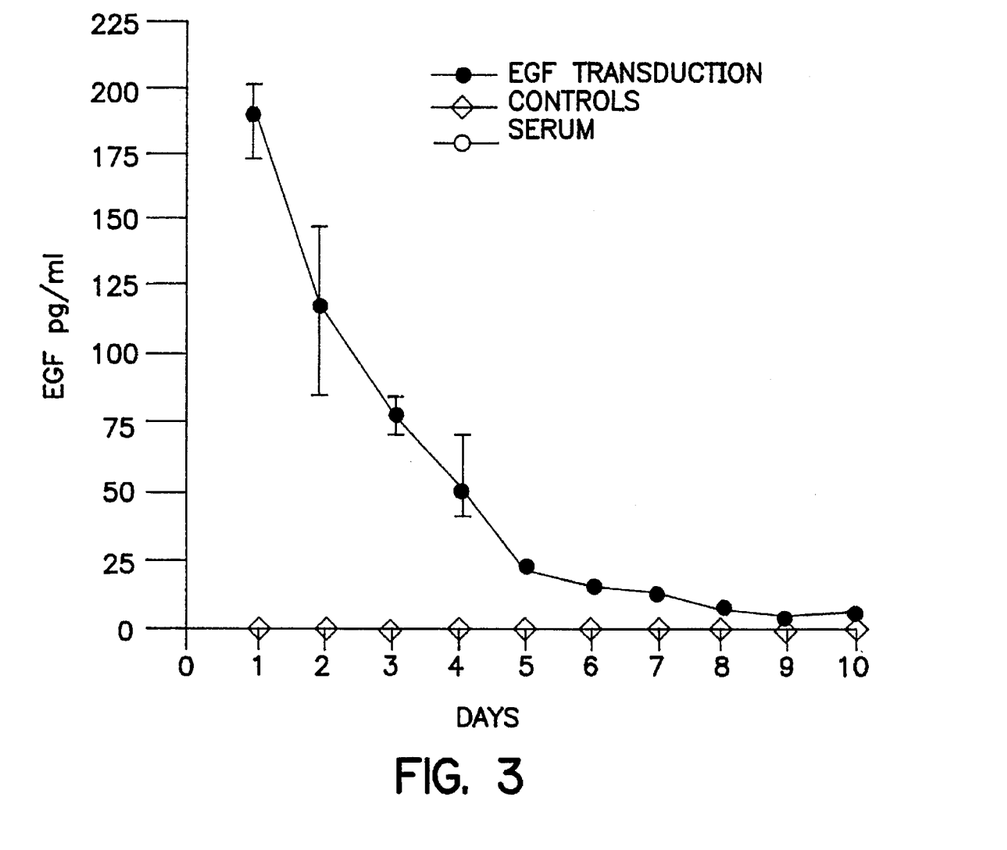
FIG. 3 depicts the levels of EGF in wound fluid as a function of time after delivery of the genetic construct of FIG. 1 into a partial thickness wound.
Figure 4:
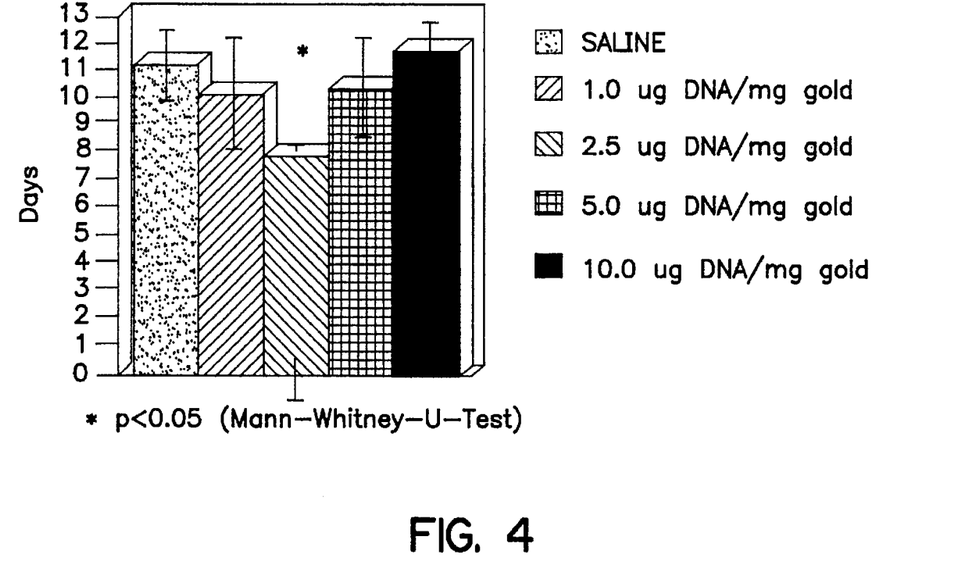
FIG. 4 depicts the healing time of partial thickness wounds after delivery of the genetic construct of FIG. 1.

FIG. 3 shows the levels of EGF measured by ELISA assay (Quartikine, R&D Systems, Minneapolis, Minn.) in wound fluid over time after particle-mediated gene transfer of 740 ng DNA per cm² of target as described. It is noted that the highest level of EGF expression was observed following delivery of this amount of DNA. The peak EGF level (approximately 190 pg/ml), observed one day after DNA delivery was 190 fold higher than the EGF level in wound fluid after delivery of the negative control. Lesser increases in EGF concentration were observed with the other DNA containing samples. The high level of EGF expression at 740 ng/cm² of target (2.5 µg of DNA per mg of gold) correlated also with a statistically significant decrease in healing times that were shortest at that DNA concentration. These results are depicted in FIG. 4.

Using standard conversion factors, one may readily determine the number of DNA molecules per µg of the 4,283 base pair pWRG1630. It is also possible to determine the number of gold beads per mg of gold from the density of gold (19.3 g/cubic cm) and the volume per bead in µ³. The beads used ranged in diameter from 1 to 3 microns. Had all the beads been 1 micron beads, a concentration of 2.5 micrograms of DNA per milligram of gold beads amounts of $4.5\times10^4$ DNA molecules per bead. Likewise, had the beads all been three micron beads, each bead would contain $3.9\times10^5$ molecules per bead. Thus, a preferred number of plasmid DNA molecules per bead is in the range of $4.5\times10^4$ to $3.9\times10^5$. However, given the limits inherent in calculating these ranges from few data points, acceptable results can likely be obtained over a broader range, such as from between $10^4$ and $10^6$ molecules per bead. Although the range was determined using plasmid pWRG1630, it is believed that the preferred density of other, comparable expressible DNA molecules would also fall within this concentration range. To deliver about 740 ng/cm², the preferred number of DNA molecules transferred is between $10^{11}$ and $10^{12}$ molecules, most preferably $5\times10^{11}$ molecules.

b. Accelerated Wound Healing

Figure 5:
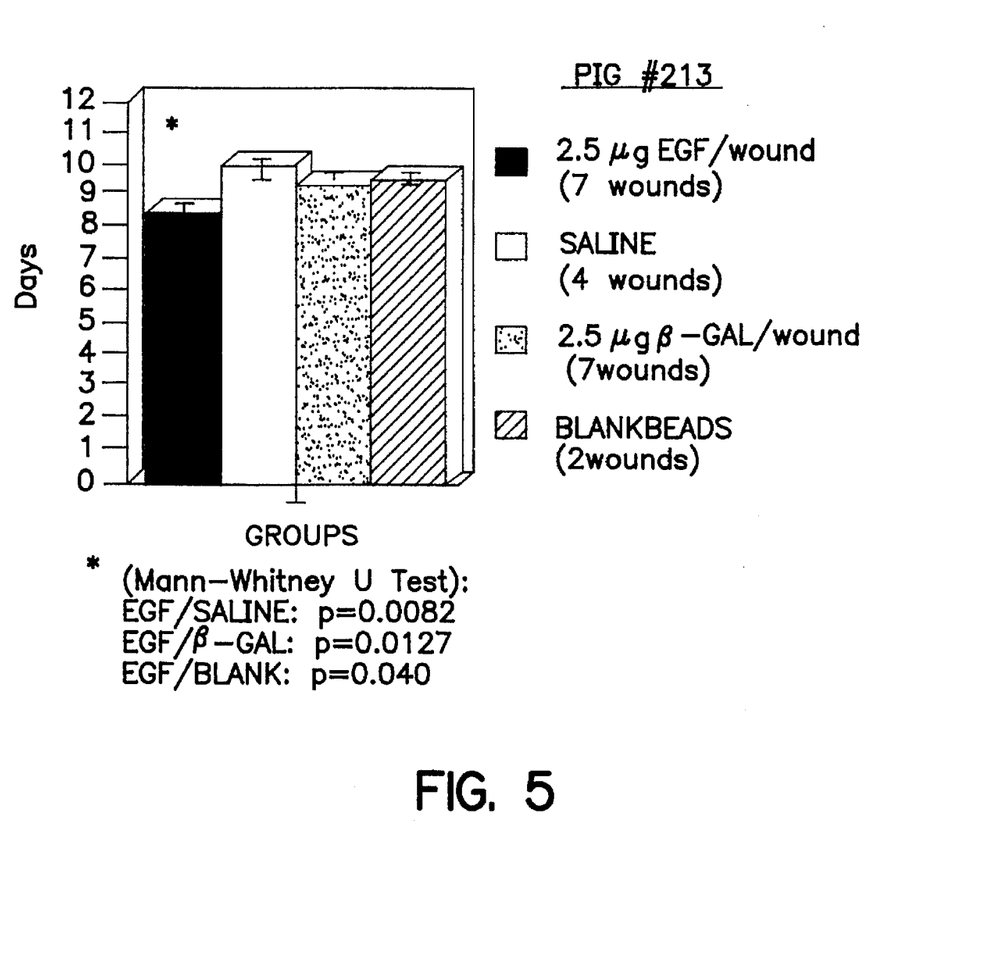
FIG. 5 compares the healing time of partial thickness wounds treated either with the genetic construct of FIG. 1 or with controls that encode no EGF.

When 740 ng were delivered as described above into partial thickness wounds on pig skin, healing was significantly accelerated. (Mann-Whitney U-Test, p<0.05) when compared to the healing times observed after delivery of control samples. The control samples included a saline control, a genetic construct similar to pWRG1630 but having a gene encoding β-galactosidase in place of the EGF coding region, and uncoated (blank) beads. This comparison of healing times is depicted in FIG. 5.

The EGF levels determined over time in this experiment were comparable to those observed after transfer of pWRG1630 in the titration experiment. Very low EGF levels were observed in wounds treated with either saline or the β-galactosidase-encoding plasmid.

High levels of EGF in wound fluid are desirable. A general correlation is observed between the level of EGF produced and the healing time of a wound. As EGF levels decrease, wound healing times increase. However, if levels get high enough (on the order of 500 pg EGF/ml), healing is slower.

These examples demonstrate the effectiveness of a DNA-mediated delivery system for mature epidermal growth factor in a wound treatment system. This system avoids the need to purify, store, and deliver EGF protein to a wound. Purified EGF is expensive to obtain and difficult to work with as a result of its short half life in the wound. On the other hand, EGF-encoding DNA is inexpensive to manufacture and store and, because it directs the continuous expression of EGF protein in treated cells, it has none of the half-life problems that attend treatment wounds with EGF protein itself. Moreover, the construct engineered and utilized by the present inventors, and other obvious modifications of this construct, avoid the processing problems associated with using the full length EGF precursor gene.

It is to be understood that the preceding examples are merely exemplary and not intended to limit the scope of the invention which encompasses all such modifications and variations as fall within the scope of the following claims.

We claim:

1. A method for treating a skin wound site on an animal, the method comprising:

coating onto a plurality of gold beads a DNA molecule that includes a non-naturally occurring gene that encodes a secretable mature epidermal growth factor, the non-naturally occurring gene consisting essentially of a coding region that encodes a mature epidermal growth factor a signal sequence that directs secretion of a protein from a skin cell, and a polyA addition sequence, the signal sequence being between the coding region and the polyA addition sequence, the DNA molecule being coated onto the gold beads in an amount sufficient to effect secretion from cells of a detectable amount of epidermal growth factor after delivery of the DNA molecule thereunto;

accelerating the coated gold beads toward and into a plurality of basal layer target skin cells at the skin wound site;

isolating the skin wound site from the external environment so that the mature epidermal growth factor secreted from the target cells contacts surrounding cells and enhances healing at the wound site relative to healing at a skin wound site into which the DNA molecule is not delivered.

2. A method as claimed in claim 1 wherein the animal is a mammal.

3. A method as claimed in claim 2 wherein the mammal is a human.

4. A method as claimed in claim 1 wherein the DNA molecule is a genetic construction comprising, in 5' to 3' order, a transcriptional promoter capable of promoting transcription in the skin cells, a signal sequence that directs secretion of a protein from the cells, a non-naturally occurring DNA fragment encoding an epidermal growth factor that lacks all coding regions of a natural epidermal growth factor precursor gene except the coding region that encodes the secretable mature epidermal growth factor, and a poly A addition sequence.

5. A method as claimed in claim 4 wherein the coding region that encodes the secretable mature epidermal growth factor region is selected from the group consisting of (1) a portion of the SmaI/SnaBI DNA fragment of λgt10EGF116 (ATCC 59956) between the MA 1 and MA 2 PCR primers, (2) the DNA sequence set forth in SEQ ID NO: 3 between nucleotides 1092 and 1253, (3) any portion of the DNA sequence set forth in SEQ ID NO: 3 between nucleotides 1092 and 1253 that encodes a polypeptide having epidermal growth enhancing activity when incorporated into the genetic construction and delivered into the cells and (4) a DNA sequence sufficiently homologous to any portion of the sequence set forth in SEQ ID NO: 3 between nucleotides 1092 and 1253 that encodes a polypeptide having epidermal growth enhancing activity when incorporated into the genetic construction and delivered into the cells, wherein the enhanced epidermal growth activity is determined relative to epidermal growth activity at a site into which the DNA sequence or the genetic construction is not delivered.

6. A method as claimed in claim 1 wherein the ratio of DNA molecules to gold beads is between $10^4$ and $10^6$ DNA molecules per gold bead.

7. A method as claimed in claim 1 wherein the ratio of DNA molecules to gold beads is between $4.5 \times 10^4$ and $3.9 \times 10^5$ DNA molecules per gold bead.

8. A method as claimed in claim 1 wherein between 300 ng and 1.5 µg of DNA are delivered per $cm^2$ of the wound site.

9. A method as claimed in claim 1 wherein the isolating step comprises surrounding the wound site with a would healing chamber.

10. A method for treating a skin wound site on an animal, the method comprising:

coating onto a plurality of gold beads a genetic construction consisting essentially of, in 5' to 3' order, a transcriptional promoter capable of promoting transcription in the skin cells, a signal sequence that directs secretion of a protein from a cell, a DNA fragment encoding a non-naturally occurring epidermal growth factor gene that lacks all coding regions of a natural epidermal growth factor precursor gene except the coding region that encodes a mature epidermal growth factor, and a poly A addition sequence, the genetic construction being coated onto the gold beads in an amount sufficient to effect secretion from the cells of a detectable amount of epidermal growth factor after delivery of the genetic construction thereunto;

accelerating the coated gold beads toward and into a plurality of basal layer target skin cells at the skin wound site;

isolating the skin wound site from the external environment so that mature epidermal growth factor secreted from the target cells contacts surrounding cells and enhances healing at the wound site relative to healing at a skin wound site into which the genetic construction is not delivered.

11. A method as claimed in claim 10 wherein the animal is a mammal.

12. A method as claimed in claim 11 wherein the mammal is a human.

13. A method as claimed in claim 10 wherein the coding region that encodes the secretable mature epidermal growth factor region is selected from the group consisting of (1) a portion of the SmaI/SnaBI DNA fragment of λgt10EGF116 (ATCC 59956) between the MA 1 and MA 2 PCR primers, (2) the DNA sequence set forth in SEQ ID NO: 3 between nucleotides 1092 and 1253, (3) any portion of the DNA sequence set forth in SEQ ID NO: 3 between nucleotides 1092 and 1253 that encodes a polypeptide having epidermal growth enhancing activity when incorporated into the genetic construction and delivered into the cells, and (4) a DNA sequence sufficiently homologous to any portion of the sequence set forth in SEQ ID NO: 3 between nucleotides 1092 and 1253 that encodes a polypeptide having epidermal growth enhancing activity when incorporated into the genetic construction and delivered into the cells, wherein the enhanced epidermal growth activity is determined relative to epidermal growth activity at a site into which the DNA sequence or the genetic construction is not delivered.

14. A method as claimed in claim 10 wherein the ratio of DNA molecules to gold beads is between $10^4$ and $10^6$ DNA molecules per gold bead.

15. A method as claimed in claim 10 wherein the ratio of DNA molecules to gold beads is between $4.5 \times 10^4$ and $3.9 \times 10^5$ DNA molecules per gold bead.

16. A method as claimed in claim 10 wherein between 300 ng and 1.5 µg of DNA are delivered per $cm^2$ of the wound site.

17. A method as claimed in claim 10 wherein the isolating step comprises surrounding the wound site with a would healing chamber.

18. A genetic construction consisting essentially of, in 5' to 3' order, a transcriptional promoter capable of promoting transcription in the skin cells, a signal sequence that directs secretion of a protein from a skin cell, a non-naturally occurring DNA fragment encoding an epidermal growth factor that lacks all coding regions of a natural epidermal growth factor precursor gene except the coding region that encodes the mature epidermal growth factor, and a poly A addition sequence.

19. A genetic construction as claimed in claim 18 wherein the coding region that encodes the mature epidermal growth factor region is selected from the group consisting of (1) a portion of the SmaI/SnaBI DNA fragment of λgt10EGF116 (ATCC 59956) between the MA 1 and MA 2 PCR primers, (2) the DNA sequence set forth in SEQ ID NO: 3 between nucleotides 1092 and 1253, (3) any portion of the DNA sequence set forth in SEQ ID NO: 3 between nucleotides 1092 and 1253 that encodes a polypeptide having epidermal growth enhancing activity when incorporated into the genetic construction and delivered into the cells and (4) a DNA sequence sufficiently homologous to any portion of the sequence set forth in SEQ ID NO: 3 between nucleotides 1092 and 1253 that encodes a polypeptide having epidermal growth enhancing activity, wherein the enhanced epidermal growth activity is determined relative to epidermal growth activity at a site into which the DNA sequence or the genetic construction is not delivered.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( C ) INDIVIDUAL ISOLATE: MA1 PCR Primer     ( x i ) SEQUENCE DESCRIPTION: SEQ ID NO:1:

```
TCAATAGTGA CTCTGAATGT CCCC                                              24
```

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( C ) INDIVIDUAL ISOLATE: MA2 PCR Primer     ( x i ) SEQUENCE DESCRIPTION: SEQ ID NO:2:

```
TCAGCGCAGT TCCCACCACT TCAG                                              24
```

( 2 ) INFORMATION FOR SEQ ID NO:3:

( i ) SEQUENCE CHARACTERISTICS:
        ( A ) LENGTH: 4283 base pairs
        ( B ) TYPE: nucleic acid
        ( C ) STRANDEDNESS: double
        ( D ) TOPOLOGY: circular     ( i i ) MOLECULE TYPE: DNA (genomic)

( v i i ) IMMEDIATE SOURCE:
        ( B ) CLONE: pWRG1630

( i x ) FEATURE:
        ( A ) NAME/KEY: exon
        ( B ) LOCATION: 713..721

( i x ) FEATURE:
        ( A ) NAME/KEY: exon
        ( B ) LOCATION: 981..1253

( i x ) FEATURE:
        ( A ) NAME/KEY: CDS
        ( B ) LOCATION: join(713..721, 981..1253)

( i x ) FEATURE:
        ( A ) NAME/KEY: sig_peptide
        ( B ) LOCATION: 713..1049

( x i ) SEQUENCE DESCRIPTION: SEQ ID NO:3:

```
GGGCGAATTC GATCCTGCAG GTCCGTTACA TAACTTACGG TAAATGGCCC GCCTGGCTGA        60
CCGCCCAACG ACCCCGCCC  ATTGACGTCA ATAATGACGT ATGTTCCCAT AGTAACGCCA       120
ATAGGGACTT TCCATTGACG TCAATGGGTG GAGTATTTAC GGTAAACTGC CCACTTGGCA       180
```

-continued

```
GTACATCAAG TGTATCATAT GCCAAGTACG CCCCTATTG  ACGTCAATGA CGGTAAATGG    240

CCCGCCTGGC ATTATGCCCA GTACATGACC TTATGGGACT TTCCTACTTG GCAGTACATC    300

TACGTATTAG TCATCGCTAT TACCATGGTG ATGCGGTTTT GGCAGTACAT CAATGGGCGT    360

GGATAGCGGT TTGACTCACG GGGATTTCCA AGTCTCCACC CCATTGACGT CAATGGGAGT    420

TTGTTTTGGC ACCAAAATCA ACGGGACTTT CCAAAATGTC GTAACAACTC CGCCCCATTG    480

ACGCAAATGG GCGGTAGGCG TGTACGGTGG GAGGTCTATA TAAGCAGAGC TCGTTTAGTG    540

AACCGTCAGA TCGCCTGGAG ACGCCATCCA CGCTGTTTTG ACCTCCATAG AAGACACCGG    600

GACCGATCCA GCCTCCGCGG CCGGGAACGG TGCATTGGAA CGGACTCTAG AGGATCCCAA    660

GGCCCAACTC CCCGAACCAC TCAGGGTCCT GTGGACAGCT CACCTAGCTG CA ATG        715
                                                            Met
                                                             1

GCT ACA GGTAAGCGCC CCTAAAATCC CTTTGGCACA ATGTGTCCTG AGGGGAGAGG       771
Ala Thr

CAGCGACCTG TAGATGGGAC GGGGGCACTA ACCCTCAGGG TTTGGGGTTC TGAATGTGAG    831

TATCGCCATC TAAGCCCAGT ATTTGGCCAA TCTCAGAAAG CTCCTGGCTC CCTGGAGGAT    891

GGAGAGAGAA AAACAAACAG CTCCTGGAGC AGGGAGAGTG TTGGCCTCTT GCTCTCCGGC    951

TCCCTCTGTT GCCCTCTGGT TTCTCCCCA GGC TCC CGG ACG TCC CTG CTC CTG    1004
                                   Gly Ser Arg Thr Ser Leu Leu Leu
                                     5                   10

GCT TTT GGC CTG CTC TGC CTG CCC TGG CTT CAA GAG GGC AGT GCC TTC    1052
Ala Phe Gly Leu Leu Cys Leu Pro Trp Leu Gln Glu Gly Ser Ala Phe
         15                  20                  25

CCA ACC ATT CCC TTA TAT CAA GCT TCG ATA TCC CGG GTT AAT AGT GAC    1100
Pro Thr Ile Pro Leu Tyr Gln Ala Ser Ile Ser Arg Val Asn Ser Asp
         30                  35                  40

TCT GAA TGT CCC CTG TCC CAC GAT GGG TAC TGC CTC CAT GAT GGT GTG    1148
Ser Glu Cys Pro Leu Ser His Asp Gly Tyr Cys Leu His Asp Gly Val
         45                  50                  55

TGC ATG TAT ATT GAA GCA TTG GAC AAG TAT GCA TGC AAC TGT GTT GTT    1196
Cys Met Tyr Ile Glu Ala Leu Asp Lys Tyr Ala Cys Asn Cys Val Val
 60              65                  70                      75

GGC TAC ATC GGG GAG CGA TGT CAG TAC CGA GAC CTG AAG TGG TGG GAA    1244
Gly Tyr Ile Gly Glu Arg Cys Gln Tyr Arg Asp Leu Lys Trp Trp Glu
         80                  85                  90

CTG CGC TGA AAACACCGTG CGGCCGCATC GATCTCGAGC ATGCATCTAG             1293
Leu Arg  *

AGGGCCCTAT TCTATAGTGT CACCTAAATG CTAGAGCTCG CTGATCAGCC TCGACTGTGC   1353

CTTCTAGTTG CCAGCCATCT GTTGTTTGCC CCTCCCCGT  GCCTTCCTTG ACCCTGGAAG   1413

GTGCCACTCC CACTGTCCTT TCCTAATAAA ATGAGGAAAT TGCATCGCAT TGTCTGAGTA   1473

GGTGTCATTC TATTCTGGGG GGTGGGGTGG GGCAGGACAG CAAGGGGGAG GATTGGGAAG   1533

ACAATAGCAG GCATGCTGGG GATGCGGTGG GCTCTATGGA ACCAGCTGGG GCTCGAGCAT   1593

GCAAGCTTGA GTATTCTATA GTGTCACCTA AATAGCTTGG CGTAATCATG GTCATAGCTG   1653

TTTCCTGTGT GAAATTGTTA TCCGCTCACA ATTCCACACA ACATACGAGC CGGAAGCATA   1713

AAGTGTAAAG CCTGGGGTGC CTAATGAGTG AGCTAACTCA CATTAATTGC GTTGCGCTCA   1773

CTGCCCGCTT TCCAGTCGGG AAACCTGTCG TGCCAGCTGC ATTAATGAAT CGGCCAACGC   1833

GCGGGGAGAG GCGGTTTGCG TATTGGGCGC TCTTCCGCTT CCTCGCTCAC TGACTCGCTG   1893

CGCTCGGTCG TTCGGCTGCG GCGAGCGGTA TCAGCTCACT CAAAGGCGGT AATACGGTTA   1953

TCCACAGAAT CAGGGGATAA CGCAGGAAAG AACATGTGAG CAAAAGGCCA GCAAAAGGCC   2013
```

```
AGGAACCGTA AAAAGGCCGC GTTGCTGGCG TTTTTCGATA GGCTCCGCCC CCCTGACGAG    2073
CATCACAAAA ATCGACGCTC AAGTCAGAGG TGGCGAAACC CGACAGGACT ATAAAGATAC    2133
CAGGCGTTTC CCCCTGGAAG CTCCCTCGTG CGCTCTCCTG TTCCGACCCT GCCGCTTACC    2193
GGATACCTGT CCGCCTTTCT CCCTTCGGGA AGCGTGGCGC TTTCTCATAG CTCACGCTGT    2253
AGGTATCTCA GTTCGGTGTA GGTCGTTCGC TCCAAGCTGG GCTGTGTGCA CGAACCCCCC    2313
GTTCAGCCCG ACCGCTGCGC CTTATCCGGT AACTATCGTC TTGAGTCCAA CCCGGTAAGA    2373
CACGACTTAT CGCCACTGGC AGCAGCCACT GGTAACAGGA TTAGCAGAGC GAGGTATGTA    2433
GGCGGTGCTA CAGAGTTCTT GAAGTGGTGG CCTAACTACG GCTACACTAG AAGGACAGTA    2493
TTTGGTATCT GCGCTCTGCT GAAGCCAGTT ACCTTCGGAA AAAGAGTTGG TAGCTCTTGA    2553
TCCGGCAAAC AAACCACCGC TGGTAGCGGT GGTTTTTTTG TTTGCAAGCA GCAGATTACG    2613
CGCAGAAAAA AAGGATCTCA AGAAGATCCT TTGATCTTTT CTACGGGGTC TGACGCTCAG    2673
TGGAACGAAA ACTCACGTTA AGGGATTTTG GTCATGAGAT TATCAAAAAG GATCTTCACC    2733
TAGATCCTTT TAAATTAAAA ATGAAGTTTT AAATCAATCT AAAGTATATA TGAGTAAACT    2793
TGGTCTGACA GTTACCAATG CTTAATCAGT GAGGCACCTA TCTCAGCGAT CTGTCTATTT    2853
CGTTCATCCA TAGTTGCCTG ACTCCCCGTC GTGTAGATAA CTACGATACG GGAGGGCTTA    2913
CCATCTGGCC CCAGTGCTGC AATGATACCG CGAGACCCAC GCTCACCGGC TCCAGATTTA    2973
TCAGCAATAA ACCAGCCAGC CGGAAGGGCC GAGCGCAGAA GTGGTCCTGC AACTTTATCC    3033
GCCTCCATCC AGTCTATTAA TTGTTGCCGG GAAGCTAGAG TAAGTAGTTC GCCAGTTAAT    3093
AGTTTGCGCA ACGTTGTTGG CATTGCTACA GGCATCGTGG TGTCACGCTC GTCGTTTGGT    3153
ATGGCTTCAT TCAGCTCCGG TTCCCAACGA TCAAGGCGAG TTACATGATC CCCCATGTTG    3213
TGCAAAAAAG CGGTTAGCTC CTTCGGTCCT CCGATCGTTG TCAGAAGTAA GTTGGCCGCA    3273
GTGTTATCAC TCATGGTTAT GGCAGCACTG CATAATTCTC TTACTGTCAT GCCATCCGTA    3333
AGATGCTTTT CTGTGACTGG TGAGTACTCA ACCAAGTCAT TCTGAGAATA GTGTATGCGG    3393
CGACCGAGTT GCTCTTGCCC GGCGTCAATA CGGGATAATA CCGCGCCACA TAGCAGAACT    3453
TTAAAAGTGC TCATCATTGG AAAACGTTCT TCGGGGCGAA AACTCTCAAG GATCTTACCG    3513
CTGTTGAGAT CCAGTTCGAT GTAACCCACT CGTGCACCCA ACTGATCTTC AGCATCTTTT    3573
ACTTTCACCA GCGTTTCTGG GTGAGCAAAA ACAGGAAGGC AAAATGCCGC AAAAAAGGGA    3633
ATAAGGGCGA CACGGAAATG TTGAATACTC ATACTCTTCC TTTTTCAATA TTATTGAAGC    3693
ATTTATCAGG GTTATTGTCT CATGAGCGGA TACATATTTG AATGTATTTA GAAAAATAAA    3753
CAAATAGGGG TTCCGCGCAC ATTTCCCCGA AAAGTGCCAC CTGACGTCTA AGAAACCATT    3813
ATTATCATGA CATTAACCTA TAAAAATAGG CGTATCACGA GGCCCTTTCG TCTCGCGCGT    3873
TTCGGTGATG ACGGTGAAAA CCTCTGACAC ATGCAGCTCC CGGAGACGGT CACAGCTTGT    3933
CTGTAAGCGG ATGCCGGGAG CAGACAAGCC CGTCAGGGCG CGTCAGCGGG TGTTGGCGGG    3993
TGTCGGGGCT GGCTTAACTA TGCGGCATCA GAGCAGATTG TACTGAGAGT GCACCATATG    4053
CGGTGTGAAA TACCGCACAG ATGCGTAAGG AGAAAATACC GCATCAGGCG CCATTCGCCA    4113
TTCAGGCTGC GCAACTGTTG GGAAGGGCGA TCGGTGCGGG CCTCTTCGCT ATTACGCCAG    4173
CTGGCGAAAG GGGGATGTGC TGCAAGGCGA TTAAGTTGGG TAACGCCAGG GTTTTCCCAG    4233
TCACGACGTT GTAAAACGAC GGCCAGTGAA TTGTAATACG ACTCACTATA              4283
```

( 2 ) INFORMATION FOR SEQ ID NO:4:

( i ) SEQUENCE CHARACTERISTICS:
  ( A ) LENGTH: 93 amino acids
  ( B ) TYPE: amino acid
  ( D ) TOPOLOGY: linear ( i i ) MOLECULE TYPE: protein ( x i ) SEQUENCE DESCRIPTION: SEQ ID NO:4:

| Met 1 | Ala | Thr | Gly | Ser 5 | Arg | Thr | Ser | Leu | Leu 10 | Leu | Ala | Phe | Gly | Leu 15 | Leu |
| Cys | Leu | Pro | Trp 20 | Leu | Gln | Glu | Gly | Ser 25 | Ala | Phe | Pro | Thr | Ile 30 | Pro | Leu |
| Tyr | Gln | Ala 35 | Ser | Ile | Ser | Arg | Val 40 | Asn | Ser | Asp | Ser | Glu 45 | Cys | Pro | Leu |
| Ser | His 50 | Asp | Gly | Tyr | Cys | Leu 55 | His | Asp | Gly | Val | Cys 60 | Met | Tyr | Ile | Glu |
| Ala 65 | Leu | Asp | Lys | Tyr | Ala 70 | Cys | Asn | Cys | Val | Val 75 | Gly | Tyr | Ile | Gly | Glu 80 |
| Arg | Cys | Gln | Tyr | Arg 85 | Asp | Leu | Lys | Trp | Trp 90 | Glu | Leu | Arg | | | |